(12) United States Patent
Hsieh

(10) Patent No.: US 6,493,416 B1
(45) Date of Patent: Dec. 10, 2002

(54) METHOD AND APPARATUS FOR NOISE REDUCTION IN COMPUTED TOMOGRAPHIC SYSTEMS

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/990,016

(22) Filed: Nov. 21, 2001

(51) Int. Cl.$^7$ ................................................. A61B 6/03
(52) U.S. Cl. ............................................ 378/4; 378/901
(58) Field of Search ............................ 378/4, 8, 15, 19, 378/901

(56) References Cited

U.S. PATENT DOCUMENTS

| | | |
|---|---|---|
| 4,761,819 A * | 8/1988 | Denison et al. ............. 382/128 |
| 5,454,019 A | 9/1995 | Migita et al. |
| 5,530,731 A | 6/1996 | Polacin et al. |
| 5,625,660 A | 4/1997 | Tuy |
| 5,626,146 A | 5/1997 | Barber et al. |
| 5,818,896 A | 10/1998 | Hsieh |
| 6,049,623 A * | 4/2000 | Fuderer et al. ............. 382/131 |
| 6,073,040 A | 6/2000 | Kiyuna |

* cited by examiner

Primary Examiner—David V. Bruce
(74) Attorney, Agent, or Firm—Carl B. Horton, Esq.; Armstrong Teasdale LLP (57) ABSTRACT

A method for facilitating a reduction in reconstructed image noise in a computed tomography imaging system. The method includes generating projection data, characterizing a noise distribution of the projection data, performing an adaptive noise reduction operation on the projection data using the noise distribution characterization, and filtering the projection data.

27 Claims, 4 Drawing Sheets

METHOD AND APPARATUS FOR NOISE REDUCTION IN COMPUTED TOMOGRAPHIC SYSTEMS

BACKGROUND OF THE INVENTION

This invention relates to tomographic imaging, and more particularly to methods and apparatus for reducing reconstructed image noise in a computerized tomographic (CT) imaging system.

In at least one known CT imaging system configuration, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In some known imaging systems, using sub-millimeter scanning speeds, the demands on the peak and sustained x-ray source power increase substantially resulting in a signal loss to the detector. Additionally, a signal loss can be caused by gaps between individual detector cells resulting in the number of detected x-ray photons decreasing by more than a factor of two thereby facilitating a reduction in image quality. Additionally, an increased x-ray dosage may produce adverse effects in a human body, therefore, a reduced x-ray photon flux facilitates a reduction in the x-ray dosage a patient receives since an x-ray dosage received by a patient should be minimized. This is generally accomplished with a reduced x-ray tube current, which typically results in a decreased number of x-ray photons.

BRIEF SUMMARY OF THE INVENTION

In one aspect, a method for facilitating a reduction in reconstructed image noise in a computed tomography imaging system is provided. The method includes generating projection data, characterizing a noise distribution of the projection data, performing an adaptive noise reduction operation on the projection data using the noise distribution characterization, and reconstructing an image.

In another aspect, a method for facilitating a reduction in reconstructed image noise in a computed tomography imaging system is provided. The method includes generating projection data, pre-processing the projection data using at least one of an offset correction, a primary speed correction, a reference channel correction, and an air-calibration. The method also includes characterizing a noise distribution of the projection data wherein characterizing a noise distribution includes generating an air calibration vector, performing a polynomial fit of the air calibration vector to generate a bowtie shape vector and approximating a standard deviation of the noise distribution using the bowtie shape vector in accordance with $$\sigma(\gamma) = \frac{B(\gamma)\sqrt{p(\gamma)}}{p(\gamma_0)}.$$

The method also includes performing an adaptive noise reduction operation on the projection data using the noise distribution characterization, filtering the projection data in accordance with $p_r(\gamma)=p(\gamma)-\alpha(\gamma)\lfloor p(\gamma)-p_f(\gamma)\rfloor$, and reconstructing an image.

In a further aspect, a computed tomographic (CT) imaging system for facilitating a reduction in reconstructed image noise is provided. The computed tomographic (CT) imaging system includes a detector array, at least one radiation source, and a computer coupled to the detector array and radiation source and configured to generate projection data. The computer is also configured to characterize a noise distribution of the projection data, perform an adaptive noise reduction operation on the projection data using the noise distribution characterization, and reconstruct an image.

In still a further aspect, a computed tomography (CT) imaging system for facilitating a reduction in reconstructed image noise is provided. The computed tomography (CT) imaging system includes a detector array, at least one radiation source, and a computer coupled to the detector array and radiation source and configured to generate projection data, pre-process the projection data using at least one of an offset correction, a primary speed correction, a reference channel correction, and an air-calibration. The computer is also configured to characterize a noise distribution of the projection data, wherein to characterize a noise distribution includes generating an air calibration vector, performing a polynomial fit of the air calibration vector to generate a bowtie shape, approximating a standard deviation of the noise distribution using the bowtie shape vector in accordance with $$\sigma(\gamma) = \frac{B(\gamma)\sqrt{p(\gamma)}}{p(\gamma_0)}.$$

The computer is also configured to perform an adaptive noise reduction operation on the projection data using the noise distribution characterization, filter the projection data in accordance with $p_r(\gamma)=p(\gamma)-\alpha(\gamma)\lfloor p(\gamma)-p_f(\gamma)\rfloor$, and reconstruct an image.

In yet another aspect, a computer readable medium encoded with a program executable by-a computer for facilitating a reduction in reconstructed image noise in a computed tomography imaging system is provided. The program is configured to instruct the computer to generate projection data, characterize a noise distribution of the projection data, perform an adaptive noise reduction operation on the projection data using the noise distribution characterization, and reconstruct an image.

In yet another further aspect, a computer readable medium encoded with a program executable by a computer for facilitating a reduction in reconstructed image noise in a computed tomography imaging system is provided. The program is configured to instruct the computer to generate projection data, pre-process the projection data using at least one of an offset correction, a primary speed correction, a reference channel correction, and an air-calibration. The program is also configured to characterize a noise distribution of the projection data wherein to characterize a noise distribution includes generating an air calibration vector, performing a polynomial fit of the air calibration vector to generate a bowtie shape vector and approximating a standard deviation of the noise distribution using the bowtie shape vector in accordance with $$\sigma(\gamma) = \frac{B(\gamma)\sqrt{p(\gamma)}}{p(\gamma_0)}.$$

(The program is also configured to instruct the computer to perform an adaptive noise reduction operation on the projection data using the noise distribution characterization, filter the projection data in accordance with $p_r(\gamma)=p(\gamma)-\alpha(\gamma)[p(\gamma)-p_f(\gamma)]$, and reconstruct an image.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
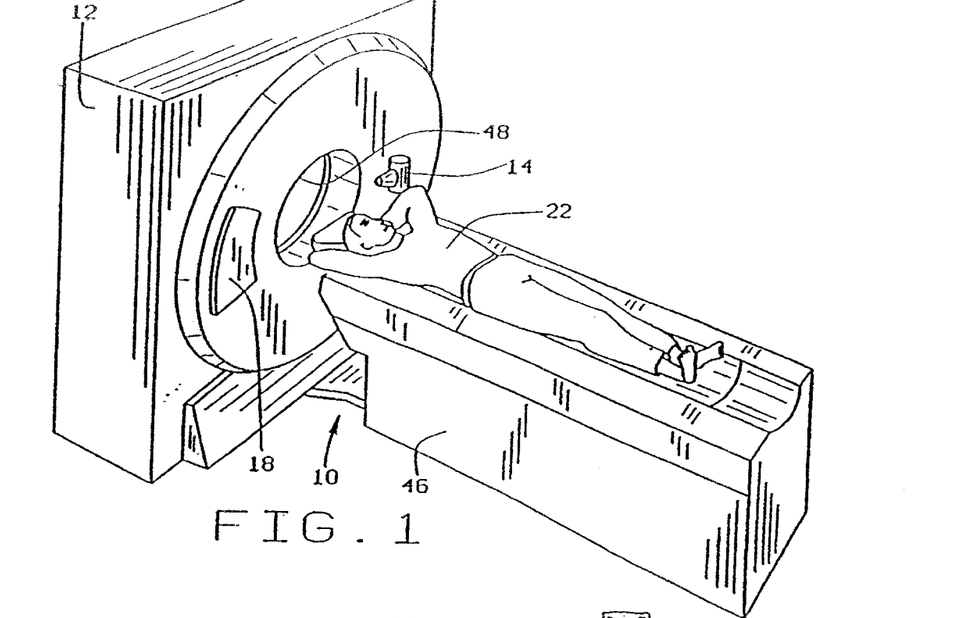
FIG. 1 is a pictorial view of a CT imaging system.
Figure 2:
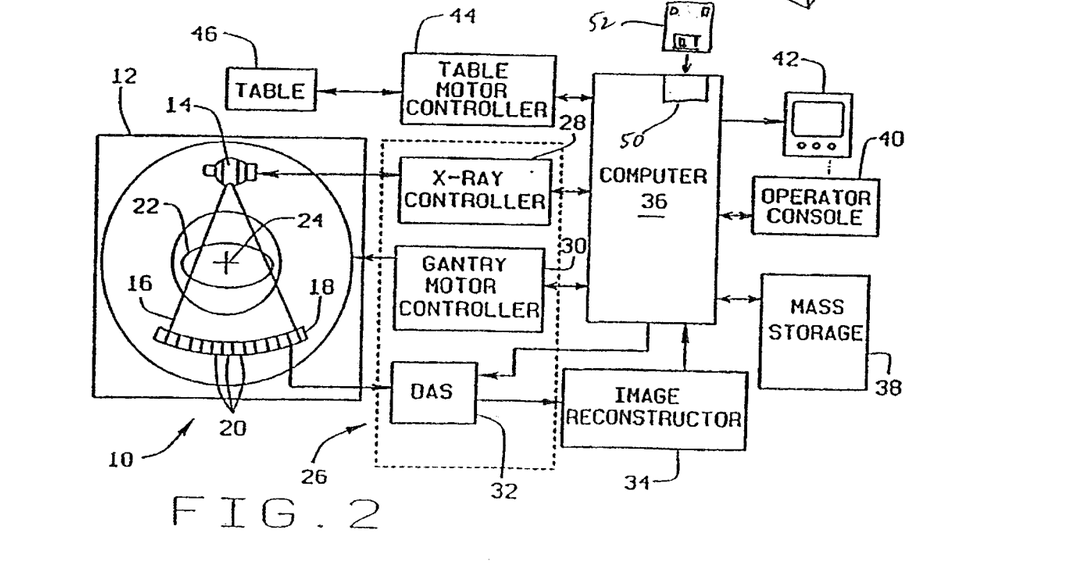
FIG. 2 is a block schematic diagram of the system illustrated in FIG. 1.

Referring to FIGS. 1 and 2, a computed tomography (CT) imaging system 10 is shown as including a gantry 12 representative of a "third generation" twin beam CT scanner. Gantry 12 has an x-ray radiation source 14 that projects a beam of x-ray radiation 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 is fabricated in a multi-slice configuration such that detector array 18 has a plurality of rows of detector elements or cells 20, only one of which is shown in FIG. 2. During a twin beam helical scan, data is acquired from two detector rows at the same time. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38. Computer 36 also receives commands and scanning parameters from an operator via console 40 that has a keyboard. An associated display 42, such as a cathode ray tube or a liquid crystal display, allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

Computer 36 and/or image reconstructor 34 of imaging system 10, either alone or in combination, provide the processing power necessary to perform the computational steps described herein in at least one embodiment of the present invention. Instructions for performing the computational steps are stored in an associated memory, such as storage device 38, read only or read/write memory (not shown separately in FIG. 1), or media 52.

One obstacle in performing smoothing operations on the projection data is the difficulty in separating the real signal variation from the statistical fluctuation. However, if certain variations in the signal caused solely by statistical noise can be pre-determined, then a low-pass filter operation can be performed on the projection data without impacting the spatial resolution. For example, the noise characteristics of the measured signal, i.e. projection data, facilitate differentiating between variations caused by the statistical fluctuation and the real structure in object 22.

Figure 3:
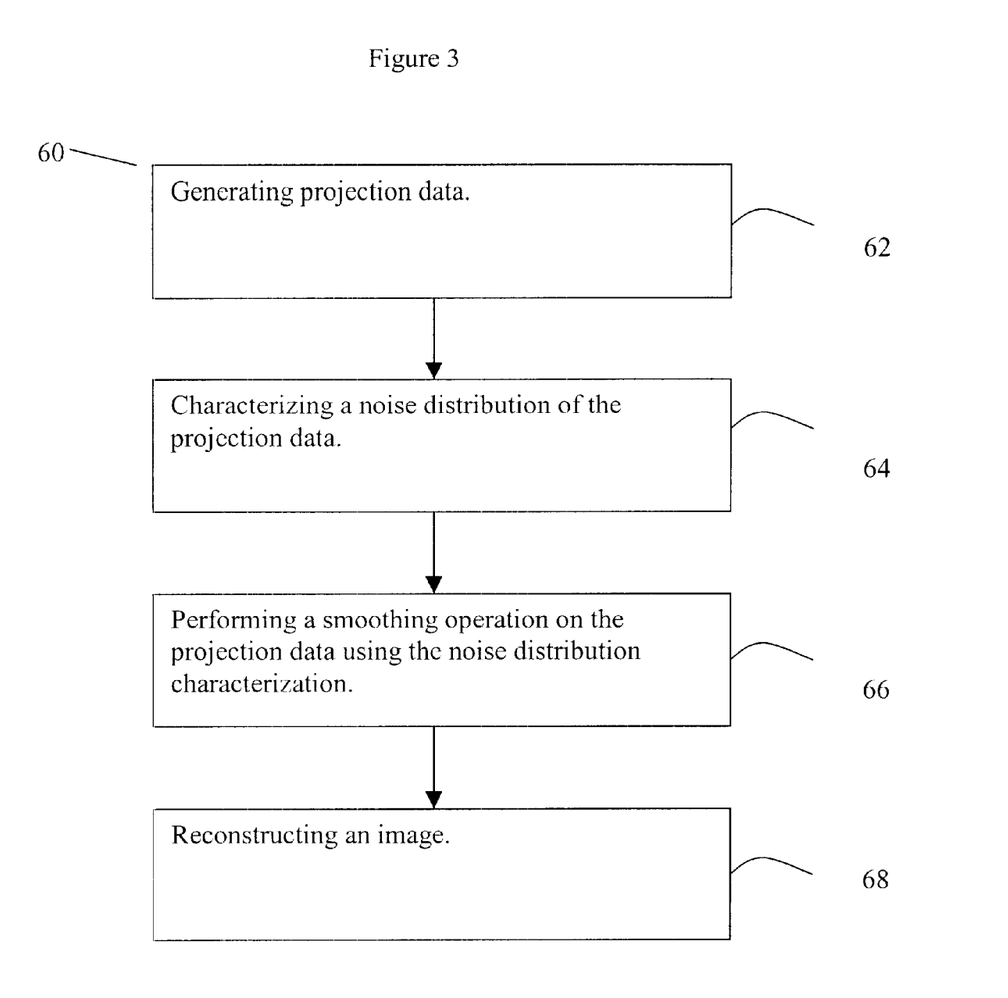
FIG. 3 is a flow diagram of a method for facilitating a reduction in reconstructed image noise.

FIG. 3 is a flow diagram of a method 60 for facilitating a reduction in statistical noise in a computed tomography imaging system. In one embodiment, the noise is a x-ray photon noise. In another embodiment, the noise is a combination of electronic noise and photon noise. Method 60 includes generating 62 projection data, characterizing 64 a noise distribution of the projection data, performing 66 an adaptive noise reduction operation on the projection data using the noise distribution characterization, and reconstructing 68 an image.

In one embodiment, generating 62 projection data includes scanning an object 22 (shown in FIG. 1) using a computed tomography (CT) imaging system 10 (shown in FIG. 1). The projection data is pre-processed. In one embodiment, pre-processing includes, but is not limited to, an offset correction, a primary speed correction, a reference channel correction, and an air-calibration. In one embodiment, the projection data is pre-processed up to the step of minus logarithm operation. Pre-processing the projection data and calibrating imaging system 10 facilitates a reduction in artifacts in the image.

Characterizing 64 a noise distribution of the projection data includes generating an air calibration vector, performing a polynomial fit of the air calibration vector to generate a bowtie shape vector, and approximating a standard deviation of the of the noise distribution using the bowtie shape vector.

In one embodiment, an air-calibration vector is generated with a bowtie filter. Therefore, the signal after air-calibration no longer represents the actual measured x-ray photon flux. A bowtie shape vector which estimates a bowtie effect is then generated. The bowtie shape vector is generated by performing a polynomial fit of the air-calibration vector in accordance with Equation 1.

$$B(\gamma) = \text{poly}_{13} \text{ fit}(x^2, \text{Aircal}(\gamma)) \qquad \text{Equation 1}$$

where $B(\gamma)$ is the bowtie shaped vector, and x is a detector channel index with an iso-channel equal to zero. In one embodiment, a fifth order polynomial fit is used. In an another embodiment, an $n^{th}$ order polynomial is used, i.e. n>5. Alternatively, the bowtie vector, $B(\gamma)$, can be determined directly from the x-ray photon flux measurement. In use, a first set of air-scans, i.e. a scan without an object inside the scanning plane, is collected with a bowtie. A second set of air scans is collected without a bowtie. The ratio of the first set of air scans and the second set of air-scans represents the bowtie vector $B(\gamma)$.

After pre-processing the projection data, the noise distribution of the projection data can be assumed to follow a Poisson distribution. Therefore, a standard deviation $\sigma(\gamma)$ of the projection data can be approximated by:

$$\sigma(\gamma) = \frac{B(\gamma)\sqrt{p(\gamma)}}{p(\gamma_0)} \qquad \text{Equation 2}$$

where $p(\gamma)$ is the calibrated projection data before minus log, and $p(\gamma_0)$ is a reference channel signal. An index for detector rows is not used since this method is identical to all rows. Similarly, for simplicity, an index for a projection angle has been omitted. In an exemplary embodiment, equation 2 is applied to every projection sample in the data set, i.e. each channel, each detector row, and each projection view.

Figure 4:
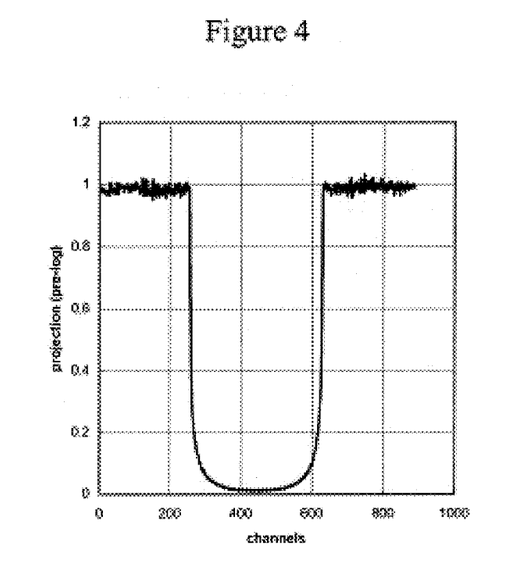
FIG. 4 is a graphical representation of a calibrated projection of a quality assurance (QA) phantom.
Figure 5:
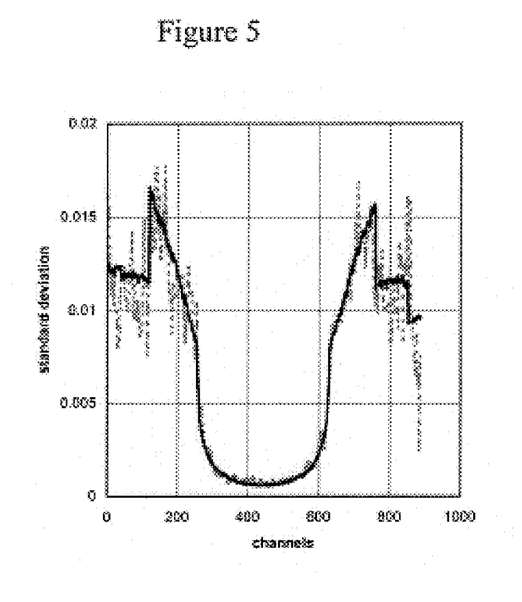
FIG. 5 is a graphical representation of the approximated standard deviation.

FIG. 4 is a graphical representation of a calibrated projection of a quality assurance (QA) phantom. FIG. 5 is a graphical representation of an approximated standard deviation based on equation (2) wherein the approximated standard deviation is represented by a solid line, and a corresponding measured standard deviation is represented by a dotted line.

Performing 66 an adaptive noise reduction operation on the projection data using the noise distribution characterization includes defining a high threshold $t_{high}$ and a low threshold $t_{low}$. If the measured variation of the projection sample over its neighborhood is less than $\sigma(\gamma)t_{low}$, a fully smoothing operation is applied. If the measured variation is greater than $\sigma(\gamma)t_{high}$, no smoothing operation is performed. When the variation is between approximately $\sigma(\gamma)t_{high}$ and $\sigma(\gamma)t_{low}$, the amount of smoothing is adjusted based on the variation level. In one embodiment, smoothing is performed on a channel-by-channel basis. The variation can be measured by calculating the standard deviation in a small region of interest. In one embodiment, a plurality of different orientations is used for the variation measurement. In one embodiment, a variance can be calculated across channels, across views, and across detector rows. In another embodiment, a plurality of intermediate directions, such as, but not limited to, diagonal across both channels, and views can be used. In a further embodiment, a plurality of multi-resolution type of approaches can be used. For example, two, three, or four adjacent detector channels can be summed to form a single channel and a variation analysis and filtering can be performed on the compressed projections.

Filtering the projection data includes filtering along the directions where the variations fall within the previously defined threshold, i.e. between $t_{low}$ and $t_{high}$. A plurality of filtering methods can be used to derive a filtered projection. For example, any type of low pass filter or statistical based filter may be used. Using the derived filtered projection, $p_f(\gamma)$ a modified projection, $p_r(\gamma)$ can be obtained according to:

$$p_r(\gamma) = p(\gamma) - \alpha(\gamma)[p(\gamma) - p_f(\gamma)] \qquad \text{Equation 3}$$

where $\alpha(\gamma)$ is determined based on the previously calculated variance and the thresholds.

Figure 6:
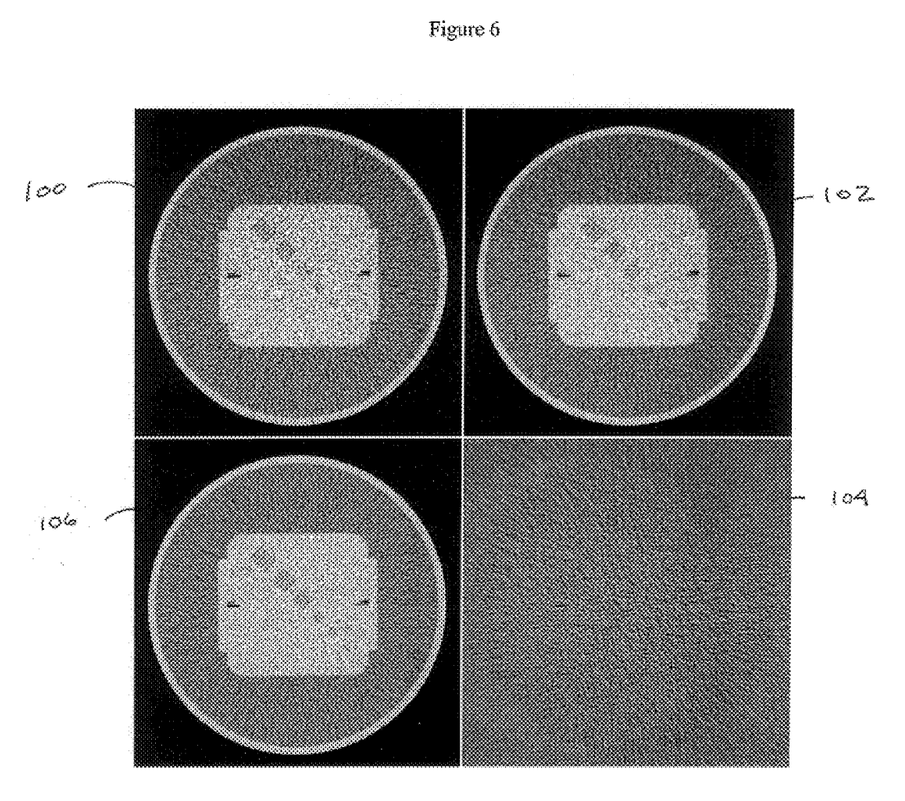
FIG. 6 is a plurality of images of a reconstructed phantom used to illustrate the effectiveness of the filtering method.

FIG. 6 is a plurality of images of a reconstructed phantom used to illustrate the effectiveness of the filtering method. Image 100 illustrates an example of a QA phantom scanned and reconstructed with a conventional reconstruction algorithm. Image 102 illustrates the same QA phantom processed in accordance with one method described herein. Image noise is significantly reduced with the adaptive processing. Image 104 illustrates is a difference image of image 100 and image 102. In one embodiment, no structural information is present in the difference image, indicating the algorithms ability to preserve spatial resolution. Image 106 illustrates a QA phantom scanned with 1.8 times the tube current and reconstructed with the conventional reconstruction algorithm. Note that the image noise level is comparable to that of image 102.

While the invention has been described in terms of various specific embodiments, those skilled in the art will recognize that the invention can be practiced with modification within the spirit and scope of the claims.

What is claimed is:

1. A method for facilitating a reduction in reconstructed image noise in a computed tomography imaging system, said method comprising:

generating projection data;

characterizing a noise distribution of the projection data;

performing an adaptive noise reduction operation on the projection data using the noise distribution characterization; and reconstructing an image.

2. A method in accordance with claim 1 further comprising pre-processing the projection data.

3. A method in accordance with claim 2 wherein pre-processing the projection data comprises pre-processing the projection data with at least one of an offset correction, a primary speed correction, a reference channel correction, and an air-calibration.

4. A method in accordance with claim 1 wherein characterizing a noise distribution of the projection data comprises:

generating an air calibration vector;

performing a polynomial fit of the air calibration vector to generate a bowtie shape vector; and approximating a standard deviation of the noise distribution using the bowtie shape vector.

5. A method in accordance with claim 1 wherein characterizing a noise distribution of the projection data comprises:

collecting a first set of air scans with a bowtie;

collecting a second set of air scans without a bowtie; and calculating the ratio of the first set of air scans and the second set of air scans to generate a bowtie vector.

6. A method in accordance with claim 1 wherein performing an adaptive noise reduction operation comprises defining a high threshold $t_{high}$ and a low threshold $t_{low}$ and fully smoothing below $\sigma(\gamma)t_{low}$ and variably smoothing between approximately $\sigma(\gamma)t_{high}$ and $\sigma(\gamma)t_{low}$.

7. A method in accordance with claim 4 wherein approximating a standard deviation of the noise distribution using the bowtie shape vector comprises approximating a standard deviation of the noise distribution in accordance with $$\sigma(\gamma) = \frac{B(\gamma)\sqrt{p(\gamma)}}{p(\gamma_0)};$$

where:

$\gamma$ is the detector angle for the projection sample of a particular view and a particular projection angle;

$\sigma(\gamma)$ is a standard deviation of the projection data with detector angle $\gamma$ for a particular detector row and projection angle;

$B(\gamma)$ is the bowtie shape vector;

$p(\gamma)$ is the calibrated projection data with detector angle $\gamma$ for a particular detector row and projection angle; and $p(\gamma_0)$ is a reference channel data.

8. A method in accordance with claim 1 further comprising filtering the projection data comprises filtering the projection data in accordance with $p_r(\gamma)=p(\gamma)-\alpha(\gamma)\lfloor p(\gamma)-p_f(\gamma)\rfloor$;

where:

$p_r(\gamma)$ is a modified projection sample with detector angle $\gamma$ for a particular detector row and projection angle;

$p_f(\gamma)$ is a filtered projection sample with detector angle $\gamma$ for a particular detector row and projection angle;

$\alpha(\gamma)$ is a parameter determined by the variation of the projection data and the threshold parameters; and $p(\gamma)$ is the calibrated projection data with detector angle $\gamma$ for a particular detector row and projection angle.

9. A method for facilitating a reduction in reconstructed image noise in a computed tomography imaging system, said method comprising:

generating projection data;

pre-processing the projection data using at least one of an offset correction, a primary speed correction, a reference channel correction, and an air-calibration;

characterizing a noise distribution of the projection data wherein said characterizing comprises:

generating an air calibration vector;

performing a polynomial fit of the air calibration vector to generate a bowtie shape vector; and approximating a standard deviation of the noise distribution using the bowtie shape vector in accordance with $$\sigma(\gamma) = \frac{B(\gamma)\sqrt{p(\gamma)}}{p(\gamma_0)};$$

where:

$\gamma$ is the detector angle for the projection sample of a particular view and a particular projection angle;

$\sigma(\gamma)$ is a standard deviation of the projection data with detector angle $\gamma$ for a particular detector row and projection angle;

$B(\gamma)$ is the bowtie shape vector;

$p(\gamma)$ is the calibrated projection data with detector angle $\gamma$ for a particular detector row and projection angle; and $p(\gamma_0)$ is a reference channel data;

performing an adaptive noise reduction operation on the projection data using the noise distribution characterization; and filtering the projection data in accordance with $p_r(\gamma)=p(\gamma)-\alpha(\gamma)\lfloor p(\gamma)-p_f(\gamma)\rfloor$;

where:

$p_r(\gamma)$ is a modified projection sample with detector angle $\gamma$ for a particular detector row and projection angle;

$p_f(\gamma)$ is a filtered projection sample with detector angle $\gamma$ for a particular detector row and projection angle;

$\alpha(\gamma)$ is a parameter determined by the variation of the projection data and the threshold parameters; and $p(\gamma)$ is the calibrated projection data with detector angle $\gamma$ for a particular detector row and projection angle; and reconstructing an image.

10. A computed tomography (CT) imaging system for facilitating a reduction in reconstructed image noise, said computed tomography (CT) imaging system comprising:

a detector array;

at least one radiation source; and a computer coupled to said detector array and radiation source and configured to:

generate projection data;

characterize a noise distribution of the projection data;

perform an adaptive noise reduction operation on the projection data using the noise distribution characterization; and reconstruct an image.

11. A computed tomography (CT) imaging system in accordance with claim 10 wherein to facilitate a reduction in reconstructed image noise in a computed tomography imaging system, said computer further configured to pre-process the projection data.

12. A computed tomography (CT) imaging system in accordance with claim 11 wherein said computer further configured to pre-process the projection data using at least one of an offset correction, a primary speed correction, a reference channel correction, and an air-calibration.

13. A computed tomography (CT) imaging system in accordance with claim 10 wherein to characterize a noise distribution of the projection data said computer further configured to:
   generate an air calibration vector;
   perform a polynomial fit of the air calibration vector to generate a bowtie shape vector; and
   approximate a standard deviation of the noise distribution using the bowtie shape vector.

14. A computed tomography (CT) imaging system in accordance with claim 10 wherein to characterize a noise distribution of the projection data said computer further configured to:
   collect a first set of air scans with a bowtie;
   collect a second set of air scans without a bowtie; and
   calculate the ratio of the first set of air scans and the second set of air scans to generate a bowtie vector.

15. A computed tomography (CT) imaging system in accordance with claim 10 wherein to perform an adaptive noise reduction operation, said computer further configured to define a high threshold $t_{high}$ and a low threshold $t_{low}$ and fully smoothing below $\sigma(\gamma)t_{low}$ and variably smoothing between approximately $\sigma(\gamma)t_{high}$ and $\sigma(\gamma)t_{low}$.

16. A computed tomography (CT) imaging system in accordance with claim 13 wherein to approximate a standard deviation of the noise distribution using the bowtie shape vector, said computer further configured to approximate a standard deviation of the noise distribution in accordance with $$\sigma(\gamma) = \frac{B(\gamma)\sqrt{p(\gamma)}}{p(\gamma_0)};$$

where:
   $\gamma$ is the detector angle for the projection sample of a particular view and a particular projection angle;
   $\sigma(\gamma)$ is a standard deviation of the projection data with detector angle $\gamma$ for a particular detector row and projection angle;
   $B(\gamma)$ is the bowtie shape vector;
   $p(\gamma)$ is the calibrated projection data with detector angle $\gamma$ for a particular detector row and projection angle; and
   $p(\gamma_0)$ is a reference channel data.

17. A computed tomography (CT) imaging system in accordance with claim 10 wherein said computer further configured to filter the projection data in accordance with $p_r(\gamma)=p(\gamma)-\alpha(\gamma)\lfloor p(\gamma)-p_f(\gamma)\rfloor$;
where:
   $p_r(\gamma)$ is a modified projection sample with detector angle $\gamma$ for a particular detector row and projection angle;
   $p_f(\gamma)$ is a filtered projection sample with detector angle $\gamma$ for a particular detector row and projection angle;
   $\alpha(\gamma)$ is a parameter determined by the variation of the projection data and the threshold parameters; and
   $p(\gamma)$ is the calibrated projection data with detector angle $\gamma$ for a particular detector row and projection angle.

18. A computed tomography (CT) imaging system for facilitating a reduction in reconstructed image noise, said computed tomography (CT) imaging system comprising:
   a detector array;
   at least one radiation source; and
   a computer coupled to said detector array and radiation source and configured to:
      generate projection data;
      pre-process the projection data using at least one of an offset correction, a primary speed correction, a reference channel correction, and an air-calibration;
      characterize a noise distribution of the projection data wherein to characterize a noise distribution comprises:
         generating an air calibration vector;
         performing a polynomial fit of the air calibration vector to generate a bowtie shape; and
         approximating a standard deviation of the noise distribution using the bowtie shape vector in accordance with $$\sigma(\gamma) = \frac{B(\gamma)\sqrt{p(\gamma)}}{p(\gamma_0)};$$

where:
   $\gamma$ is the detector angle for the projection sample of a particular view and a particular projection angle;
   $\sigma(\gamma)$ is a standard deviation of the projection data with detector angle $\gamma$ for a particular detector row and projection angle;
   $B(\gamma)$ is the bowtie shape vector;
   $p(\gamma)$ is the calibrated projection data with detector angle $\gamma$ for a particular detector row and projection angle; and
   $p(\gamma_0)$ is a reference channel data;
      perform an adaptive noise reduction operation on the projection data using the noise distribution characterization;
      filter the projection data in accordance with $p_r(\gamma)=p(\gamma)-\alpha(\gamma)\lfloor p(\gamma)-p_f(\gamma)\rfloor$;
      where:
         $p_r(\gamma)$ is a modified projection sample with detector angle $\gamma$ for a particular detector row and projection angle;
         $p_f(\gamma)$ is a filtered projection sample with detector angle $\gamma$ for a particular detector row and projection angle;
         $\alpha(\gamma)$ is a parameter determined by the variation of the projection data and the threshold parameters; and
         $p(\gamma)$ is the calibrated projection data with detector angle $\gamma$ for a particular detector row and projection angle, and
      reconstruct an image.

19. A computer readable medium encoded with a program executable by a system for facilitating a reduction in reconstructed image noise in a computed tomography imaging system, said program configured to instruct the computer to:
   generate projection data;
   characterize a noise distribution of the projection data;
   perform an adaptive noise reduction operation on the projection data using the noise distribution characterization; and
   reconstruct an image.

20. A computer readable medium in accordance with claim 19 wherein to facilitate a reduction in reconstructed image noise in a computed tomography imaging system, said program further configured to pre-process the projection data.

21. A computer readable medium in accordance with claim 20 wherein said program further configured to pre-process the projection data using at least one of an offset correction, a primary speed correction, a reference channel correction, and an air-calibration.

22. A computer readable medium in accordance with claim 19 wherein to characterize a noise distribution of the projection data said program further configured to:
   generate an air calibration vector;
   perform a polynomial fit of the air calibration vector to generate a bowtie shape vector; and
   approximate a standard deviation of the noise distribution using the bowtie shape vector.

23. A computer readable medium in accordance with claim 19 wherein to characterize a noise distribution of the projection data said program further configured to:
   collect a first set of air scans with a bowtie;
   collect a second set of air scans without a bowtie; and
   calculate the ratio of the first set of air scans and the second set of air scans to generate a bowtie vector.

24. A computer readable medium in accordance with claim 19 wherein to perform an adaptive noise reduction operation, said program further configured to define a high threshold $t_{high}$ and a low threshold $t_{low}$ and fully smooth below $\sigma(\gamma)t_{low}$ and variably smooth between approximately $\sigma(\gamma)t_{high}$ and $\sigma(\gamma)t_{low}$.

25. A computer readable medium in accordance with claim 22 wherein to approximate a standard deviation of the noise distribution using the bowtie shape vector, said program further configured to approximate a standard deviation of the noise distribution in accordance with $$\sigma(\gamma) = \frac{B(\gamma)\sqrt{p(\gamma)}}{p(\gamma_0)};$$

where:
   $\gamma$ is the detector angle for the projection sample of a particular view and a particular projection angle;
   $\sigma(\gamma)$ is a standard deviation of the projection data with detector angle $\gamma$ for a particular detector row and projection angle;
   $B(\gamma)$ is the bowtie shape vector;
   $p(\gamma)$ is the calibrated projection data with detector angle $\gamma$ for a particular detector row and projection angle; and
   $p(\gamma_0)$ is a reference channel data.

26. A computer readable medium in accordance with claim 19 wherein said program further configured to filter the projection data in accordance with $p_r(\gamma)=p(\gamma)-\alpha(\gamma)[p(\gamma)-p_f(\gamma)]$;
where:
   $p_r(\gamma)$ is a modified projection sample with detector angle $\gamma$ for a particular detector row and projection angle;
   $p_f(\gamma)$ is a filtered projection sample with detector angle $\gamma$ for a particular detector row and projection angle;
   $\alpha(\gamma)$ is a parameter determined by the variation of the projection data and the threshold parameters; and
   $p(\gamma)$ is the calibrated projection data with detector angle $\gamma$ for a particular detector row and projection angle.

27. A computer readable medium encoded with a program executable by a computer for facilitating a reduction in reconstructed image noise in a computed tomography imaging system, said program configured to instruct the computer to:
   generate projection data;
   pre-process the projection data using at least one of an offset correction, a primary speed correction, a reference channel correction, and an air-calibration;
   characterize a noise distribution of the projection data wherein to characterize a noise distribution comprises:
      generating an air calibration vector;
      performing a polynomial fit of the air calibration vector to generate a bowtie shape vector; and
      approximating a standard deviation of the noise distribution using the bowtie shape vector in accordance with $$\sigma(\gamma) = \frac{B(\gamma)\sqrt{p(\gamma)}}{p(\gamma_0)};$$

where:
      $\gamma$ is the detector angle for the projection sample of a particular view and a particular projection angle;
      $\sigma(\gamma)$ is a standard deviation of the projection data with detector angle $\gamma$ for a particular detector row and projection angle;
      $B(\gamma)$ is the bowtie shape vector;
      $p(\gamma)$ is the calibrated projection data with detector angle $\gamma$ for a particular detector row and projection angle; and
      $p(\gamma_0)$ is a reference channel data;
   perform an adaptive noise reduction operation on the projection data using the noise distribution characterization;
   filter the projection data in accordance with $p_r(\gamma)=p(\gamma)-\alpha(\gamma)[p(\gamma)-p_f(\gamma)]$;
   where:
      $p_r(\gamma)$ is a modified projection sample with detector angle $\gamma$ for a particular detector row and projection angle;
      $p_f(\gamma)$ is a filtered projection sample with detector angle $\gamma$ for a particular detector row and projection angle;
      $\alpha(\gamma)$ is a parameter determined by the variation of the projection data and the threshold parameters; and
      $p(\gamma)$ is the calibrated projection data with detector angle $\gamma$ for a particular detector row and projection angle; and
   reconstruct an image.

* * * * *